United States Patent [19]

Burch et al.

[11] Patent Number: 4,619,928

[45] Date of Patent: Oct. 28, 1986

[54] COMPOSITIONS FOR TREATING TUMORS

[75] Inventors: Homer A. Burch; Frank F. Ebetino, both of Norwich, N.Y.

[73] Assignee: Norwich Eaton Pharmaceuticals, Inc., Norwich, N.Y.

[21] Appl. No.: 683,850

[22] Filed: Dec. 20, 1984

[51] Int. Cl.⁴ .......................................... A61K 31/535
[52] U.S. Cl. .................................................. 514/236
[58] Field of Search .................... 424/248.55; 514/236

[56] References Cited

PUBLICATIONS

Snyder and Ebetino, "A New Synthesis of Furo[2,3-b]-Pyridine Derivatives (1)", *The Journal of Heterocyclic Chemistry*, vol. 3 (1966), pp. 202–205.

Manske and Holmes, "III. The Furoquinoline Group," *The Alkaloids*, vol. III, Academic Press, Inc., New York, N.Y. (1953), pp. 69–71.

Ebetino et al., "Reduction of Nitrofurans. I. Aminofurans," *J. Med. Pharm. Chem.*, vol. 5 (1962), pp. 513–524.

Paul et al., "Metabolism of the Nitrofurans. I. Ultraviolet Absorption Studies of Urinary End-Products After Oral Administration", *J. Biol. Chem.*, vol. 180 (1949), pp. 345–363.

Bender and Paul, "Metabolism of the Nitrofurans. II. Incubation of Furacin with Mammalian Tissues," *J. Biol. Chem.*, vol. 191 (1951) pp. 217–222.

Taylor et al., "Metabolism of the Nitrofurans. III. Studies with Xanthine Oxidase in Vitro," *J. Biol. Chem.*, vol. 191 (1951) pp. 223–231.

Paul et al., "Metabolic Degradation of the Nitrofurans," *J. Med. Pharm. Chem.*, vol. 2 (1960) pp. 563–584.

Olivard et al., "The Metabolism of 5-Nitro-2-Furaldehyde Acetylhydrazone," *J. Med. Pharm. Chem.*, vol. 5 (1962) pp. 524–531.

Beckett and Robinson, "The Reactions of Nitrofurans with Bacteria-II.", *J. Med. Pharm. Chem.*, vol. 1 (1959) pp. 135–154.

Beckett and Robinson, "The Reaction of Nitrofurans with Bacteria-III", *J. Med. Pharm. Chem.*, vol. 1 (1959) pp. 155–164.

Chemical Abstracts 65:5435h (1966) along with the index which set forth the compound.

*Primary Examiner*—Jerome D. Goldberg
*Attorney, Agent, or Firm*—Kim William Zerby; Milton B. Graff, IV; Steven J. Goldstein

[57] ABSTRACT

The invention involves compositions useful for treating certain malignant tumors with the compound ethyl 4-hydroxy-2-[(5-morpholinomethyl-2-oxo)-3-oxazolidinyliminomethyl]furo[2,3-b]pyridine-5-carboxylate (Compound I) or its pharmaceutically acceptable salts or hydrates.

1 Claim, No Drawings

COMPOSITIONS FOR TREATING TUMORS

TECHNICAL FIELD

This invention is concerned with compositions useful for treating certain malignant tumors. More particularly it is concerned with compositions comprising the compound ethyl 4-hydroxy-2-[(5-morpholinomethyl-2-oxo)-3-oxazolidinyliminomethyl]furo[2,3-b]pyridine-5-carboxylate (Compound I) and its pharmaceutically acceptable salts and/or hydrates.

BACKGROUND OF THE INVENTION

The testing of new chemicals against tumors in rodents as a test system to discover new antitumor drugs has been facilitated by the development of the ability to transplant animal tumors, including human tumors, in such rodents. Such test systems form the backbone of cancer drug development programs today. (See DeVita, V. T., V. T. Oliverio, F. M. Muggia, P. W. Wiernik, J. Zeigler, A. Goldin, D. Rubin, J. Henney, and S. Schepartz, "The Drug Development and Chemical Trials Programs of the Division of Cancer Treatment, National Cancer Institute", *Cancer Clin. Trials*, Vol. 2 (1979), pp. 195–216; and Goldin, A., and J. M. Vendetti, "The New NCI Screen and Its Implication for Clinical Evaluation", *Recent Results in Cancer Research*, Vol. 70 (1980), S. K. Carter and Y. Sakurai (ed.), Springer-Verlag, Berlin, Germany.

Compound (I) and a method of synthesizing it are disclosed in the following reference: Snyder, H. R., Jr., and F. F. Ebetino, "A New Synthesis of Furo[2,3-b]pyridine Derivatives (1)", *The Journal of Heterocyclic Chemistry*, Vol. 3 (1966), pp. 202–205, the contents of which is hereby incorporated by reference. Compound (I) is identified as compound XVIII in this reference.

SUMMARY OF THE INVENTION

It is an object of the present invention to provide novel compositions in dosage form for treating certain malignant tumors.

The present invention relates to a method of treating certain malignant tumors comprising the administration of an effective but nontoxic amount of Compound (I) or a pharmaceutically acceptable salt and/or hydrate thereof.

DETAILED DESCRIPTION OF THE INVENTION

The present invention relates to the activity against certain malignant tumors of ethyl 4-hydroxy-2-[(5-morpholinomethyl-2-oxo)-3-oxazolidinyliminomethyl]-furo[2,3-b]pyridine-5-carboxylate (Compound I) having the chemical structure:

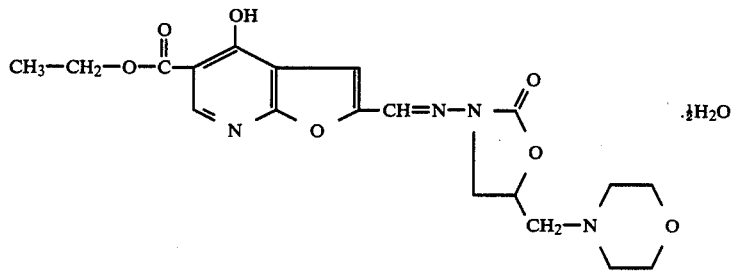

(I)

It has been found that Compound (I) possess substantial activity against certain malignant tumors. The activity was demonstrated through the employment of antitumor screening tests in mice into which the following tumors had been transplanted: P388 lymphocytic leukemia, B16 melanocarcinoma, L1210 lymphoid leukemia, Lewis lung carcinoma and colon 38 tumor. The protocols used to carry out the antitumor tests are found in the publication: Geran, R. I., N. H. Greenberg, M. M. MacDonald, A. M. Schumacher, and B. J. Abbott, "Protocols for Screening Chemical Agents and Natural Products Against Animal Tumors and Other Biological Systems", *Cancer Chemotherapy Reports*, Part 3, Vol. 3, No. 2 (September 1972), 3rd Ed.

The activity of Compound (I) against the tumors implanted in mice was measured by the increased life span (ILS) or the tumor growth inhibition (TGI) exhibited by such mice to which Compound (I) was administered compared to such mice which received no Compound (I). Compound I was generally administered as an aqueous saline suspension by intraperitoneal (i.p.) or subcutaneous (s.c.) injection or as an acidified aqueous silane solution by i.p. or intravenous (i.v.) injection for a certain numbers of days after implantation of the tumor in mice.

Compound (I) exhibited substantial activity against B16 melanoma transplanted in mice by i.p. injection. Compound (I) suspension was i.p. administered to the mice in a quantity of 200 mg/kg body weight/day on days 1–9 after transplanting the tumor. In two separate tests, the ILS of mice to which Compound (I) was administered increased 30% and 29%.

Compound (I) exhibited substantial activity against L1210 leukemia tumors which were implanted in mice either by i.p or s.c injection. In separate tests a suspension of Compound (I) was i.p. administered to mice at quantities of 200 mg/kg/day and 400 mg/kg/day on days 1–9 after transplanting of the tumors in the mice. The ILS of the mice to which Compound (I) was administered was increased by 60% at both dosage levels. Similarly, Compound (I) exhibited substantial activity against L1210 leukemia tumors transplanted in mice by s.c. injection. Compound (I) was i.p. administered to the mice as a solution on days 1–9 after transplanting of the tumors. The solution was made by dissolving Compound (I) in a 0.1N HCl saline solution. The ILS of the mice to which Compound (I) was administered increased 71% for those treated with the solution.

Compound (I) exhibited substantial activity against Lewis lung carcinoma transplanted in mice by i.v. injection. A suspension of Compound (I) was i.p. administered to mice in a quantity of 200 mg/kg/day on days 1–9 following transplanting of the tumors. The ILS of the mice which were administered Compound (I) increased 40% and 41% in two separate tests.

Compound (I) exhibited substantial activity against P388 leukemia tumors transplanted in mice by i.p. injection. A solution of Compound (I) was i.p. administered to mice at a quantity of 200 mg/kg/day on days 1–5 following transplanting of the tumors. The ILS of mice to which Compound (I) was administered increased 40%.

Compound (I) exhibited substantial activity against colon 38 tumors transplanted in mice by s.c. injection. In two separate tests, a suspension of Compound (I) was administered to mice at levels of 900 mg/kg/day and 600 mg/kg/day on days 2–9 after transplanting the tumors. The TGI of mice to which Compound (I) was administered was 66% and 71%, respectively, for the two tests.

Other furo[2,3-b]pyridines have been tested for antitumor activity in one or more of the above tests, but none have exhibited substantial activity; such compounds include the following: diethyl 4-hydroxyfuro[2,3-b]pyridine-2,5-dicarboxylate, diethyl 4-methoxyfuro[2,3-b]pyridine-2,5-dicarboxylate, diethyl-4-chlorofuro[2,3-b]pyridine-2,5-dicarboxylate, 4-hydroxyfuro[2,3-b]pyridine-2,5-dicarboxylic acid, ethyl 5-nitrofuro[2,3-b]pyridine-2-carboxylate, diethyl furo[2,3-b]pyridine-2,5-dicarboxylate, ethyl N-[2-(2-dimethylaminoethyl)carbamyl]furo[2,3-b]pyridine-5-carboxylate hydrochloride, ethyl 5-aminofuro[2,3-b]pyridine-2-carboxylate hydrochloride, diethyl 4-mercaptofuro[2,3-b]pyridine-2,5-carboxylate, and ethyl 4-hydroxy-6-trifluoromethylfuro[2,3-b]pyridine-2-carboxylate.

Certain intermediates in the synthesis of Compound I have also been tested for antitumor activity in one or more of the above tests, but none have exhibited substantial activity; such intermediates include the following: N-(5-nitrofurfurylidene)-3-amino-5-(N'-morpholinylmethyl)-2-oxazolidinone, 3-[[5-amino-2-furanyl)methylene]amino]-5-(4-morpholinylmethyl)-2-oxazolidinone, and diethyl 2-[5-(4-morpholinyl)methyl]2-oxo-3-oxazolidinyliminomethyl)-2-furanylaminomethylene]propanedioate.

The i.p. administration of Compound (I) at a level of 200 mg/kg/day was not found to provide substantial activity against CD8F$_1$ mammary tumor implanted in mice by s.c. injection. Similarly, s.c. administration of a suspension of Compound (I) at 200 mg/kg/day did not provide substantial activity against CX-1 colon tumor, LX-1 lung tumor, or MX-1 mammary tumor which were implanted beneath the renal capsule in athymic mice.

The treatment regimens encompassed by the present invention employ compositions comprising an effective but nontoxic amount of Compound (I) or its pharmaceutically acceptable salts and/or hydrates. The phrases "effective but nontoxic amount of Compound (I)", herein, means sufficient amount of Compound (I) to desirably affect and inhibit the growth of certain maligbenefit/risk ratio. Pharmaceutically acceptable salts and/or hydrates of Compound (I) include the organic and inorganic acid salts of Compound (I) which are suitable for use in contact with living tissue of animals without undue toxicity, irritation, allergic response, and the like, commensurate with a reasonable benefit/risk ratio. Such salts of Compound (I) may be formed from various inorganic acids, for example, hydrochloric acid, sulfuric acid, phosphoric acid and organic acids such as maleic acid, tartaric acid, citric acid, and the like. A preferred salt of Compound (I) is the hydrochloride salt.

Compositions comprising Compound (I) may be administered by injection (e.g. i.p., i.v., or s.c.), intravenous infusion, suppositories, and oral administration thereof, as well as by topical application of the compositions.

Within the scope of sound medical judgment, the dosage of Compound (I) used in the present invention will vary with the severity and nature of the particular condition being treated, the duration of treatment, the adjunct therapy used, and like factors within the specific knowledge and expertise of the sound medical judgment. Daily dosages can typically range from about 10 to about 2,000 mg/kg of body weight, preferably from about 50 to about 1,000 mg/kg of body weight, more preferably from about 200 to about 900 mg/kg of body weight.

Dosage compositions of the present invention comprise a safe and effective amount of Compound (I), or a pharmaceutically acceptable salt and/or hydrate thereof, and a pharmaceutical carrier. Pharmaceutical carriers include solid or liquid filler, diluent or encapsulating substances. Some examples of the substances which can serve as pharmaceutical carriers are sugars, such as lactose, glucose and sucrose; starches, such as corn starch and potato starch; cellulose and its derivatives, such as sodium carboxymethyl cellulose and its derivatives, such as sodium carboxymethyl cellulose, ethyl cellulose, cellulose acetate; powdered tragacanth; malt; gelatin; talc; stearic acid; magnesium stearate; calcium sulfate; vegetable oils, such as peanut oil, cottonseed oil, sesame oil, olive oil, corn oil and oil of theobroma; polyols, such as propylene glycol, glycerin, sorbitol, mannitol, and polyethylene glycol; agar; alginic acid; pyrogen-free water; isotonic saline; and phosphate buffer solutions; as well as non-toxic, compatible substances used in pharmaceutical formulations. Wetting agents, lubricants, such as sodium lauryl sulfate, as well as coloring agents, flavoring agents, tableting agents, and preservatives, can also be present. Tableting and encapsulating is done using conventional techniques.

The pharmaceutical carrier employed in conjunction with Compound (I) is used at a concentration sufficient to provide a practical size to dosage relationship. Preferably, the pharmaceutical carrier comprises from

EXAMPLE I

Gelatin capsules are prepared by conventional methods, as follows:

| Ingredients | Milligrams per Capsule |
| --- | --- |
| Compound (I) | 400 |
| Starch | 50 |

EXAMPLE II

Tablets are prepared by conventional methods, formulated as follows:

| Ingredient | Milligrams per Tablet |
| --- | --- |
| Compound (I) | 200 |
| Lactose | 40 |
| Starch | 3 |
| Magnesium stearate | 1 |

EXAMPLE III

Aqueous saline suspensions for parenteral or oral administration may be prepared by dispersing from about 0.1% to about 10% of Compound (I) in a physiological saline solution. The resulting suspension may be sterilized by standard sterilization techniques.

EXAMPLE IV

Solutions for parenteral or oral administration may be prepared by adding dilute (e.g. 0.1N) HCl dropwise to the suspensions of Example III until Compound (I) is dissolved. The final pH may be below 6.5. The resulting solution may be sterilized by standard sterilization techniques.

What is claimed is:

1. A pharmaceutical composition, in a dosage form selected from sterile solutions, suspensions, suppositories, tablets or capsules, comprising from about 10 mg to about 2000 mg of the compound ethyl 4-hydroxy-2-((5-morpholinomethyl-2-oxo)-3-oxazolidinyliminomethyl)-furo(2,3-b)pyridine-5-carboxylate, or a pharmaceutically-acceptable salt or hydrate or mixture thereof, and a pharmaceutical carrier.

* * * * *

UNITED STATES PATENT AND TRADEMARK OFFICE
CERTIFICATE OF CORRECTION

PATENT NO. : 4,619,928

DATED : October 28, 1986

INVENTOR(S) : Homer A. Burch and Frank F. Ebetino

It is certified that error appears in the above-identified patent and that said Letters Patent are hereby corrected as shown below:

In the specification, Column 2, line 21, "silane" should read --saline--.

Signed and Sealed this

Thirty-first Day of May, 1988

Attest:

DONALD J. QUIGG

Attesting Officer

Commissioner of Patents and Trademarks